United States Patent [19]

Hutchings et al.

[11] Patent Number: 5,162,598

[45] Date of Patent: Nov. 10, 1992

[54] CONVERSION OF PROPANE AND BUTANE

[75] Inventors: Graham J. Hutchings, Osmotherley, England; Themistoclis Themistocleous, Bryanston; Richard G. Copperthwaite, Johannesburg, both of South Africa

[73] Assignee: Zeofuels Research (Proprietary) Limited, Transvaal, South Africa

[21] Appl. No.: 815,627

[22] Filed: Dec. 30, 1991

Related U.S. Application Data

[62] Division of Ser. No. 683,411, Apr. 10, 1991, abandoned.

[30] Foreign Application Priority Data

Apr. 10, 1990 [ZA] South Africa ............... 90/2722

[51] Int. Cl.$^5$ ................................. C07C 4/02
[52] U.S. Cl. .................... 585/651; 585/653; 502/60
[58] Field of Search ........... 585/650, 651, 653, 648, 585/652; 502/60

[56] References Cited

U.S. PATENT DOCUMENTS

| | | | |
|---|---|---|---|
| 3,367,884 | 2/1968 | Reid, Jr. ................... | 502/78 |
| 3,553,278 | 1/1971 | Sato et al. ................. | 502/64 |
| 3,997,474 | 12/1976 | Miale et al. | |
| 4,059,543 | 11/1977 | Kiovsky et al. ............. | 502/60 |
| 4,172,856 | 10/1979 | Spencer et al. | |
| 4,623,529 | 11/1986 | Sanders et al. ............. | 423/328 |
| 4,956,515 | 9/1990 | Kolts et al. ................ | 585/651 |
| 4,983,560 | 1/1991 | Copperthwaite et al. ..... | 502/85 |

FOREIGN PATENT DOCUMENTS

| | | | |
|---|---|---|---|
| A0307239 | 3/1989 | European Pat. Off. | |
| 307239 | 3/1989 | European Pat. Off. ..... | 423/328 |
| 55-47143 | 4/1980 | Japan ............................ | 423/328 |
| A829655 | of 0000 | U.S.S.R. | |
| 641983 | 1/1979 | U.S.S.R. ....................... | 502/85 |
| 284245 | 5/1929 | United Kingdom ............ | 502/85 |

OTHER PUBLICATIONS

Barrer et al. "Molecular Sieve Sorbents from Clinoptlolite" Can. J. Chem. 42 (1964) pp. 1481–1487.

*Primary Examiner*—R. Bruce Breneman
*Attorney, Agent, or Firm*—Cushman, Darby & Cushman

[57] ABSTRACT

A modified natural clinoptilolite, produced by treating a natural clinoptilolite with a suitable mineral acid or with a suitable alkali and then with a suitable mineral acid, is used as a catalyst in a process for the conversion of propane or butane to give a product containing at least 40% of ethene, propene or $C_4$ hydrocarbons or a mixture thereof.

7 Claims, No Drawings

CONVERSION OF PROPANE AND BUTANE

This is a division of application Ser. No. 07/683,411, filed on Apr. 10, 1991.

BACKGROUND OF THE INVENTION

This invention relates to the use of a modified natural clinoptilolite as a catalyst in a process for the conversion of propane and butane.

Synthetic zeolite catalysts have been used for many years in the chemical and petrochemical industry; for example, Zeolite Y is used in hydrocarbon cracking processes. More recently it has been found that the synthetic Zeolite ZSM-5, suitably modified, e.g., by the addition of zinc or gallium compounds, can convert propane and butane into hydrocarbons rich in benzene, toluene and xylenes. This process, known as the CYCLAR process (which is referred to in a paper presented at the N.P.R.A. Annual Meeting, San Antonio, Tex., March 1987, J. A. Johnston, J. A. Weiszmann, G. K. Hiler and A. H. Hall) is useful in the preparation of high octane gasoline from propane and butane. This conversion process does not yield high selectivities to ethene and propene. The chemical industry would prefer a process, and thus a catalyst for the process, which results in the formation of ethene and propene as well as $C_4$ hydrocarbons, as these products are more flexible for further use. Further, the ZSM-5 zeolite catalyst is expensive and produces a very broad product range of aromatic compounds which are of poor suitability for use as chemical feedstocks.

SUMMARY OF THE INVENTION

According to a first aspect of the invention there is provided a modified natural clinoptilolite for use as a catalyst in a process for the conversion of propane or butane to give a product containing at least 40% by weight of ethene, propene or $C_4$ hydrocarbons or a mixture of two or more thereof.

The modified natural clinoptilolite may be used to catalyse the conversion of propane to give a product rich in ethene and $C_4$ hydrocarbons or to catalyse the conversion of butane to produce a product rich in ethene and propene.

The modified natural clinoptilolite may be produced starting from any suitable natural clinoptilolite such as that from Zululand, South Africa, or that from Futatsui, Japan, by any suitable modification process. Various modification processes are set out below.

According to a second aspect of the invention there is provided a process for the conversion of propane to give a product containing at least 40% of ethene or $C_4$ hydrocarbons or a mixture thereof or the for conversion of butane to give a product containing at least 40% by weight of ethene or propene or a mixture thereof, in a reactor in the presence of a modified natural clinoptilolite which includes the steps of:

(a) feeding the propane or the butane to the reactor containing the catalyst;

(b) converting the propane or the butane to ethene or $C_4$ hydrocarbons, or ethene or propene respectively, in the reactor in the presence of the catalyst at a temperature of from 400° C. to 800° C. inclusive, preferably from 450° C. to 600° C. inclusive and at a pressure of from 1 to 20 atmospheres inclusive, preferably from 1 to 5 atmospheres inclusive; and (c) recovering the product.

DESCRIPTION OF EMBODIMENTS

The first aspect of the invention is a modified natural clinoptilolite for use as a catalyst in a process for the conversion of propane to give a product containing at least 40% of ethene, $C_4$ hydrocarbons or a mixture thereof, or butane to give a product containing at least 40% of ethene, propene or a mixture thereof.

There are various processes by which the natural clinoptilolite may be modified to render it suitable for use as a catalyst, and these processes are set out below.

The first method is that disclosed in an article in Applied Catalysis, 16 (1985) 249-253, by Sakoh, Nitta and Aomura. This article discloses two methods for the modification of a natural clinoptilolite from Futatsui, Japan. The first method involves treating the natural clinoptilolite with 1M HCl at 80° C. for 24 hours after which the sample is filtered off, washed with distilled water and dried in air. The second method involves impregnating the clinoptilolite with 0.05M and 0.5M $H_2SO_4$, whereafter the samples are filtered off, dried in air and then calcined at 400° C. for 3 hours in air. These catalysts were utilised in the conversion of methanol to light olefins in a fixed bed continuous flow reactor under atmospheric pressure.

The second method is disclosed in South African Patent No 88/6733. This patent discloses a method for the modification of a natural clinoptilolite to produce a modified clinoptilolite for use in a reaction for the preparation of or transformation of hydrocarbons which method includes the step of treating the natural clinoptilolite with a suitable mineral acid such as hydrochloric acid at a concentration of greater than 1M, preferably from greater than 1M up to and including 2.5M, more preferably 2M, for a treatment time of longer than 24 hours, and at a suitable treatment temperature, preferably of from 40° C. to 80° C., to produce the modified clinoptilolite. Further, after the acid treatment step, the clinoptilolite is preferably calcined at a suitable calcining temperature, e.g. from 450° C. to 550° C., more preferably 500° C., for a suitable calcining time, e.g. 3 or 4 hours. The modified catalyst so produced may be used in a process for the conversion of methanol and/or dimethyl ether to hydrocarbon reaction products, and in a process for the cracking of hydrocarbon products.

The third method is disclosed in South African Patent No. 89/3131. This patent discloses a method for the modification of a natural clinoptilolite to produce a modified clinoptilolite for use in a reaction for the preparation of hydrocarbons, which method includes the step of treating the natural clinoptilolite with a phosphorous containing acid such as phosphoric acid, pyrophosphoric acid, metaphosphoric acid, hypophosphorous acid, phosphorous acid or pyrophosphorous acid, at a concentration of 0.5M or greater, preferably from 0.5M up to and including 2M, for a treatment time of equal to or longer than 24 hours, preferably up to and including 96 hours, and at a suitable treatment temperature, preferably of from 40° C. to 80° C. inclusive, to produce the modified clinoptilolite. After the acid treatment step, the modified clinoptilolite may be calcined at a suitable calcining temperature of from 400° C. to 550° C. for a suitable calcining time from 3 hours, more preferably 4 hours. The modified clinoptilolite so produced may be used in a process for the conversion of methanol and/or dimethyl ether to hydrocarbon reaction products.

The fourth method is disclosed in South African Patent No 89/3132. This patent discloses a method for the modification of a natural zeolite to produce a modified zeolite for use in a reaction for the transformation of hydrocarbons which method includes the steps of treating the natural zeolite with a suitable alkali such as sodium hydroxide at a concentration greater than 0.5M preferably a concentration from 0.5M up to and including 5M, more preferably 2M, for a treatment time of longer than 1 hour preferably up to and including 48 hours, and at a suitable treatment temperature preferably from 30° C. to 80° C. inclusive, washing the resulting product, and treating the resulting product with a suitable mineral acid such as hydrochloric acid at a concentration of greater than 0.1M preferably a concentration from longer than 0.1M up to and including 2M, for a treatment time of longer than 1 hour, preferably up to and including 48 hours, and at a suitable treatment temperature preferably from 40° C. to 80° C. inclusive, to produce the modified zeolite. Thereafter, the modified zeolite is preferably calcined at a suitable calcining temperature of from 400° C. to 500° C. for a suitable calcining time from 3 hours.

In terms of the present invention, the natural clinoptilolite may be modified by any of the methods described above or by any other suitable known method. The modified clinoptilolite may be produced starting from a natural clinoptilolite mined in Zululand, South Africa, or Fututsui, Japan, or from any other suitable natural clinoptilolite.

The second aspect of the invention is a process for the conversion of propane or butane to produce a product containing at least 40% of ethene, propene, or $C_4$ hydrocarbons or a mixture thereof in a reactor in the presence of a modified natural clinoptilolite which includes the steps of:

(a) feeding the propane or butane to the reactor containing the catalyst;

(b) converting the propane or butane to ethene, propene or $C_4$ hydrocarbons in the reactor in the presence of the catalyst at a temperature of from 400° C. to 800° C. inclusive, preferably from 450° C. to 600° C. inclusive, and at a pressure of from 1 to 20 atmospheres inclusive, preferably from 1 to 5 atmospheres inclusive; and (c) recovering the product.

The conversion of propane and butane to hydrocarbon products is well known and may be carried out according to the method of the present invention using the known reaction conditions.

The reaction will generally be carried out in a fixed bed or a fluidized bed reactor at the temperatures and pressures mentioned above.

Examples which illustrate the invention will now be given.

EXAMPLE 1

A sample (50 g) of unmodified natural clinoptilolite was suspended with stirring in a solution (500 ml) of 2M sodium hydroxide at 50° C. for eight houurs. Following this treatment the sample was collected by filtration and washed with de-ionised water. The sample was then suspended with stirring in 0.5M aqueous hydrochloric acid (500 ml) at 60° C. for 15 hours. The sample was collected by filtration and washed with de-ionised water, and dried at 120° C. for 4 hours, then calcined at 400° C. for 4 hours. The modified clinoptilolite was then used as a catalyst for butane conversion in a fixed bed downflow glass microreactor. Butane was reacted over the modified clinoptilolite at a weight hourly space velocity (WHSV) of 1.2 $h^{-1}$ at 550° C. Products were collected and analysed by standard gas chromatographic techniques. The results are given in Table 1 and demonstrate that the modified clinoptilolite is an effective catalyst for this process. Similar experiments in the absence of the modified clinoptilolite catalyst demonstrated that some conversion of the butane was possible, but higher conversions were obtained by using the modified clinoptilolite catalyst.

TABLE 1

Conversion of Butane over a Modified Clinoptilolite Catalyst, 500° C., WHSV = 1.2 $h^{-1}$

| TIME ON LINE (min) | 20 | 225 | 665 |
|---|---|---|---|
| Conversion of butane % | 29.4 | 18.1 | 15.7 |
| Product Selectivity % by mass | | | |
| $CH_4$ | 11.1 | 12.8 | 11.5 |
| $C_2H_4$ | 18.6 | 15.8 | 13.4 |
| $C_2H_6$ | 16.5 | 14.2 | 11.9 |
| $C_3H_6$ | 27.8 | 31.1 | 29.4 |
| $C_3H_8$ | 23.2 | 25.2 | 33.2 |
| $C_5$ | 1.8 | 0.5 | 0.3 |
| $C_6$ | 0.5 | 0.2 | 0.2 |
| $C_7$ | 0.4 | 0.1 | 0.1 |
| $C_{8+}$ | 0.1 | trace | trace |
| TOTAL $C_2H_4 + C_3H_6$ | 46.4 | 46.9 | 42.8 |

EXAMPLE 2

A sample of unmodified natural clinoptilolite was modified according to the procedure given in Example 1. The modified clinoptilolite was then used as a catalyst for propane conversion using the procedure as described in Example 1. Propane was reacted over the modified clinoptilolite at 550° C. and a WHSV of 0.9 $h^{-1}$. The results, shown in Table 2, demonstrate that the modified clinoptilolite is effective for the conversion of propane to ethene and $C_4$ hydrocarbons. Similar experiments in the absence of the modified clinoptilolite catalyst demonstrated that some conversion of the propane was possible, but higher conversions were obtained using the modified clinoptilolite catalyst.

TABLE 2

Conversion of Propane over Modified Clinoptilolite at 500° C. and WHSV = 0.9 $h^{-1}$

| TIME ON LINE (min) | 22 | 206 | 326 |
|---|---|---|---|
| Propane Conversion % | 11.6 | 7.0 | 6.6 |
| Product Selectivity % by mass | | | |
| $CH_4$ | 9.4 | 10.4 | 10.2 |
| $C_2H_4$ | 20.5 | 19.5 | 19.9 |
| $C_2H_6$ | 5.0 | 7.8 | 8.2 |
| $C_4$ | 43.1 | 53.5 | 54.3 |
| $C_5$ | 1.9 | 1.4 | 1.3 |
| $C_6$ | 4.8 | 4.3 | 4.3 |
| $C_7$ | 0.2 | 2.0 | 1.8 |
| $C_{8+}$ | 15.1 | 1.1 | 1.0 |
| TOTAL $C_2H_4 + C_4\%$ | 63.6 | 73.0 | 74.2 |

We claim:

1. A process for the conversion of propane to give a product containing at least 40% by weight ethene or $C_4$ hydrocarbons or a mixture thereof in a reactor in the presence of a modified natural clinoptilolite catalyst produced by treating a natural clinoptilolite with either (1) a mineral acid at a concentration of greater than 1M for a treatment time of longer than 24 hours or (2) alkali at a concentration greater than 0.5M for a treatment time of longer than 1 hour, washing the resulting product, and treating the resulting product with a mineral acid at a concentration of greater than 0.1M for a treatment time of longer than 1 hour which includes the steps of:
  (a) feeding the propane to the reactor containing the catalyst;
  (b) converting the propane to ethene or $C_4$ hydrocarbons or a mixture thereof in the reactor in the presence of the catalyst at a temperature of from 400° C. to 800° C. inclusive and a pressure of from 1 to 20 atmospheres inclusive; and
  (c) recovering the product.

2. A process for the conversion of butane to give a product containing at least 40% by weight of ethene or propene or a mixture thereof in a reactor in the presence of a modified natural clinoptilolite catalyst produced by treating a natural clinoptilolite with either (1) a mineral acid at a concentration of greater than 1M for a treatment time of longer than 24 hours or (2) alkali at a concentration greater than 0.5M for a treatment time of longer than 1 hour, washing the resulting product and treating the resulting product with a mineral acid at a concentration of greater than 0.1M for a treatment time of longer than 1 hour which includes the steps of:
  (a) feeding the butane to the reactor containing the catalyst;
  (b) converting the butane to ethene or propene or a mixture thereof in the reactor in the presence of the catalyst at a temperature of from 400° C. to 800° C. inclusive, and at a pressure of from 1 to 20 atmospheres inclusive; and
  (c) recovering the product.

3. A process according to claim 1 or 2 wherein the modified clinoptilolite is produced by treating the natural clinoptilolite with hydrochloric acid at a concentration of from greater than 1M up to and including 5M for a treatment time of longer than 24 hours and at a treatment temperature of from 40° C. to 80° C. inclusive.

4. A process according to claim 1 or 2 wherein the modified clinoptilolite is produced by treating a natural clinoptilolite with sodium hydroxide at a concentration of from greater than 0.5M up to and including 5M, for a treatment time of longer than 1 hour up to and including 48 hours and at a treatment temperature of 30° C. to 80° C. inclusive, washing the resulting product, and treating the resulting product with hydrochloric acid at a concentration of greater than 0.1M up to and including 2M for a treatment time of longer than 1 hour up to and including 48 hours and at a treatment temperature of from 40° C. to 80° C.

5. A process according to claim 1 or 2 wherein the modified clinoptilolite is calcined at a calcining temperature of from 400° C. to 500° C. inclusive for a calcining time of from 3 hours.

6. A process according to claim 4 wherein the modified clinoptilolite is calcined at a calcining temperature of from 400° C. to 500° C. inclusive for a calcining time of from 3 hours.

7. A process according to claim 1 or 2 wherein the modified natural clinoptilolite is produced starting from a natural clinoptilolite from Zululand, South Africa.

* * * * *